United States Patent
Bay et al.

(10) Patent No.: US 8,027,986 B2
(45) Date of Patent: Sep. 27, 2011

(54) INDICATION-DEPENDENT CONTROL ELEMENTS

(75) Inventors: Susanne Bay, Erlangen (DE); Christoph Braun, Rosenheim (DE); Hanna Köhler, Bergisch Gladbach (DE); Marcela De Castro Esteves, Princeton, NJ (US)

(73) Assignee: Siemens Aktiengesellschaft, Munich (DE)

( * ) Notice: Subject to any disclaimer, the term of this patent is extended or adjusted under 35 U.S.C. 154(b) by 512 days.

(21) Appl. No.: 12/216,822

(22) Filed: Jul. 11, 2008

(65) Prior Publication Data
US 2009/0030946 A1    Jan. 29, 2009

(30) Foreign Application Priority Data
Jul. 19, 2007  (DE) .......................... 10 2007 033 756

(51) Int. Cl.
*G06F 7/00*    (2006.01)
*G06F 17/30*    (2006.01)
(52) U.S. Cl. ............. 707/758; 707/915; 705/2; 715/764
(58) Field of Classification Search .................. 707/758, 707/915; 705/2; 715/764
See application file for complete search history.

(56) References Cited

U.S. PATENT DOCUMENTS

| 6,081,267 | A  | * | 6/2000 | Stockham et al. | 715/788 |
|---|---|---|---|---|---|
| 6,261,300 | B1 |   | 7/2001 | Carol |  |
| 2001/0051881 | A1 | * | 12/2001 | Filler | 705/3 |
| 2003/0146942 | A1 | * | 8/2003 | Helgason et al. | 345/968 |
| 2004/0078215 | A1 | * | 4/2004 | Dahlin et al. | 705/2 |
| 2005/0228250 | A1 | * | 10/2005 | Bitter et al. | 600/407 |
| 2007/0038070 | A1 |   | 2/2007 | Tank |  |
| 2007/0078678 | A1 | * | 4/2007 | DiSilvestro et al. | 705/2 |

FOREIGN PATENT DOCUMENTS

| DE | 69524434 | 8/2002 |
|---|---|---|
| DE | 103 46 410 | 5/2005 |
| EP | 1769771 | 4/2007 |

OTHER PUBLICATIONS

Office Action for German patent application No. 10 2007 033 756.8 dated Oct. 20, 2010.

* cited by examiner

*Primary Examiner* — John E Breene
*Assistant Examiner* — Phong Nguyen
(74) *Attorney, Agent, or Firm* — Harness, Dickey & Pierce, P.L.C.

(57) ABSTRACT

A method is disclosed for controlling the display of activation elements for tools for editing medical data on a user interface in a computer-based, medico-technical system. In at least one embodiment, the activation elements are displayed in an activation element area, divided into various segments, of the user interface on the basis of the medical context. The doctor is thus able to select the tools clearly on a task- or indication-specific basis without an image data area of the user interface being concealed by the activation elements.

16 Claims, 1 Drawing Sheet

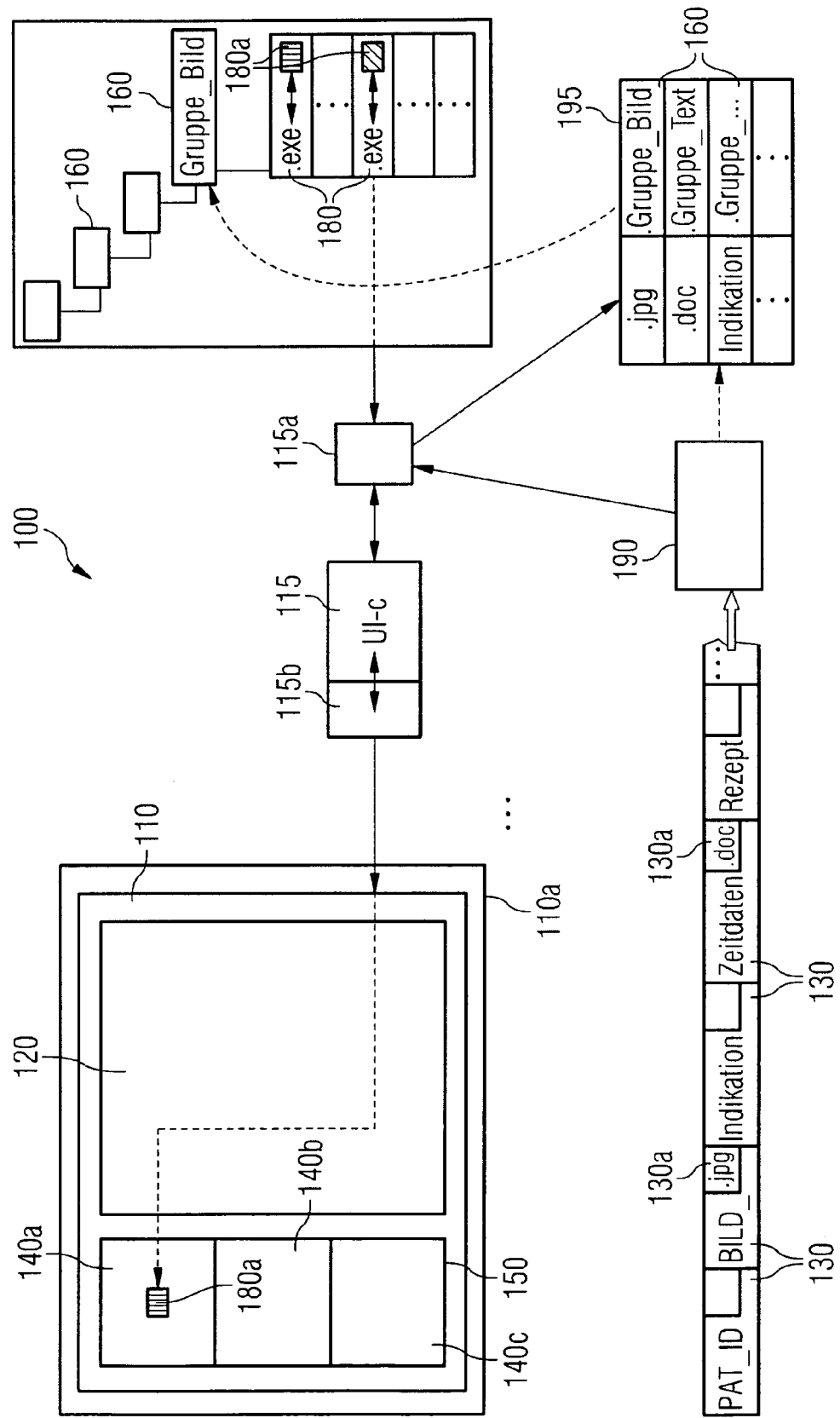

INDICATION-DEPENDENT CONTROL ELEMENTS

PRIORITY STATEMENT

The present application hereby claims priority under 35 U.S.C. §119 on German patent application number DE 10 2007 033 756.8 filed Jul. 19, 2007, the entire contents of which is hereby incorporated herein by reference.

FIELD

Embodiments of the present invention are generally in the field of medical data processing and may particularly concern graphical screen interfaces from computer-based medico-technical systems for processing medical data. Embodiments of the present invention may relate particularly to a method, to a system, a UI controller and/or a product for controlling a user interface in a computer-based medico-technical system.

BACKGROUND

In hospitals, clinics or other medical facilities, it is standard for the doctor to use a wealth of medical appliances to treat patients or to perform other tasks. The medical appliances themselves are usually controlled using computer systems. The computer systems e.g. PCs, provide a series of in some cases highly specialized tools, also called medical applications.

DE 695 24 434 and EP 1 769 771 each show an example of a graphical user interface in a respective single medical application. The medical application in DE 695 24 434 shows a control application for an apparatus for neurosurgical interventions. EP 1 769 771 shows an application for computer-aided display of a workflow for orthopedic surgical interventions.

These tools are controlled using control elements, to be more precise activation elements, which are displayed on the computer system's user interface. On account of the large number of tools available, it is not possible to present all the activation elements on the user interface. This lack of space on the user interface is also aggravated by the fact that generally not only activation elements are displayed but also the medical data to be edited.

To date, the space problem on the user interface has been solved by displaying only those activation elements which are used frequently. Activation elements which are used less often are frequently not displayed directly. In this case, the doctor needs to use a menu, for example, for selection and to operate a button or to use further options (e.g. a mouse click). By contrast, some systems are adaptive and place frequently used tools onto the directly accessible user interface after some time, while other systems provide use configuration, for example, so that each user, that is to say the doctor, for example, can himself decide which tools he wishes to access directly.

However, the previous methods for providing activation elements on the user interface have a series of drawbacks. Thus, the search for activation elements which are not displayed is highly time consuming, in particular. In addition, the current context which prompts the doctor to use a particular tool is not utilized or taken into account. The current context is generally provided through clinical questioning or a medical indication.

By way of example, one could imagine a doctor who, upon taking on a patient in casualty, needs to make a quick diagnosis and uses a medical appliance (e.g. a tomograph), to quickly obtain information about the indication. In this case, it is crucially important to find tools used for the diagnosis quickly. There is thus the problem that the wealth of tools available means that quick and efficient editing of medical data is made difficult. Since the medical context, that is to say the clinical questioning or the medical indication, is not taken into account for providing the tool, inefficiency arises in the use of the medical appliances—the information provided by the medical context lies idle and is not used for providing the tools in anticipatory fashion on the basis of this medical context.

Another problem is to present the medical data, e.g. the images, together with the activation elements such that the activation elements do not conceal or cover the images.

Another problem can also be seen as being that the aforementioned problems need to be solved using the capabilities of the existing IT infrastructure. The resultant cost saving is desirable directly in view of the strained budget of medical facilities (health insurance funds, hospitals, doctors' practices).

SUMMARY

In at least one embodiment of the present invention, an inexpensive way of generating a user interface for using medical appliances is generated, which allows medical data to be edited quickly, efficiently and securely. In addition, in at least one embodiment, a (G)UI (Graphical User Interface) controller is desirable which controls the user interface and allows context-dependent arrangement of activation elements for medical tools on the user interface.

In at least one embodiment of the present invention, a context-dependent "instrument panel" is provided for using the medico-technical appliance for processing medical data. In this case, the context is derived from the medical data themselves.

At least one embodiment of the method is described below. Features, alternative embodiments and/or advantages mentioned in this regard can similarly also be transferred to the other claimed articles, and vice versa. In other words, the material claims can also be developed with the features which are described or claimed in connection with the method. The relevant functional features of the method are in this case formed by appropriate material modules, particularly hardware and/or software modules, of the system.

At least one embodiment of the method is for controlling a user interface in a computer-based, medico-technical system, having an image data area for displaying medical data and an activation element area, divided into segments, for displaying grouped activation elements, wherein a respective segment of the activation element area is associated with a respective group of activation elements and the activation element is intended for activating a tool associated with it, the method comprising:

capture of the medical data, that is to say particularly automatic capture of data relating to the patient, for example containing a clinical indication for a patient;

determination of which tools are required for processing the captured medical data;

presentation of the activation elements associated with the required tools in that segment of the activation element area which is associated with the respective activation element, wherein the division of the activation elements is based on division of the tools associated with the respective activation elements, the tools being divided in respect of medico-technical tasks or in respect of an indication.

The terminology of the terms used in embodiments of the present invention will be described briefly below.

Control of the user interface is intended to be understood to mean all measures which are taken in relation to the visual design of the user interface. In particular, it is to be understood to mean the arrangement or geometrical positioning of control elements, buttons, also called icons. It is also meant to be understood to mean the change in the graphical design of the user interface upon interaction with the doctor, that is to say when the doctor inputs data into the system.

The term "system" is subsequently used for a combination of medico-technical appliances, such as tomographs or X-ray appliances, with a computer system which is used to operate or control the medico-technical appliances. Alternatively, a network of peripheral devices, such as external databases etc., which store the medical data to be processed, are intended to be considered to be part of the system.

Medical data generally comprise all information relating to a patient, preferably in electronic form, this information including particularly a patient's ID, information about medical history, clinical indications and data such as images, e.g. X-ray images, on the basis of which the patient may need to be treated further.

In line with one embodiment of the invention, however, meta data, which describes the medical data, are also intended to be considered to be part of the medical data. Meta data are data which describe the medical data in more detail, e.g. in what file format a particular data item is present as part of the medical data.

"User interface" generally means a graphical user interface which allows the user, in this case, the doctor, to interact with the system.

"Activation elements" comprise control elements, buttons, which are embedded in the user interface and present graphical symbols for (executable) reference files which can be used to reference or activate other files, particularly the tools, or to initiate program execution. Reference files are also known by the name "link".

"Tools" are intended to be understood to mean general but also highly specialized computer-based applications for processing medical data. Examples are image editing tools, which can be used to present images in different colors, for example. However, a tool may also be a control instrument for an external appliance (for example an appliance which is used during an operation and is controlled by means of a user interface).

"Capture" means the download to a buffer store or at least the referencing of the medical data by the system. In line with one embodiment, it is also conceivable at this juncture for the medical data to be "parsed" for further processing. The patient-related medical data can normally be found as electronic data records on external databases which are integrated in a local or regional HIS (Hospital Information System) system. One aspect of the inventive solution can be seen as being that a dynamically adapted user interface can be generated automatically and solely on the basis of the data and/or the meta data (usually using the format in which the data are present).

Determination covers all steps which relate to analysis of the captured medical data. The result of this analysis is the setup of a reference to suitably appearing tools. The information regarding which tools are suitable for which types of data is preferably preconfigurable and stored in the system. By way of example, the analysis may consist in filtering the medical data according to headwords or according to file endings. The former would be an example of the use of the medical data per se, while the latter represents use of the meta data. The medical data are captured in the form of files and the presence of a specific file format is chosen as the basis for a decision regarding which tool needs to be associated with the medical data. The file ending ".jpg" is indication, by way of example, that the file format is an image file, so that a reference to an image processing tool can be setup. On the other hand, the medical data can also be filtered using indication-specific keywords and on this basis appropriate tools referenced, however.

In line with at least one embodiment of the invention, the presentation of the required tools is an operation which involves the activation elements associated with the tool being captured and being geometrically arranged on the user interface such that they appear in a previously stipulated region of the user interface. This region is a previously stipulated but configurable segment of the activation element area. Thus, the doctor always knows precisely where on the user interface it is possible to find which context-dependent tools. For example if he needs tools for navigation on the time axis because a running examination is involved then the doctor knows that a tool which is suitable for such a task can be found in the "task-specific tools" segment.

In line with at least one embodiment of the invention, all tools provided in the medico-technical system are divided into groups. In this regard, it has been found to be advantageous for the day-to-day running of a clinic for the division to be into task-specific, indication-specific or general groups. Since each tool has an associated activation element, the grouping of the tools automatically also results in appropriate grouping of the activation elements.

In line with another embodiment of the invention, the multiplicity of the groups in which the tools are classified is implemented by an appropriate hierarchic directory structure, e.g. on a central server. In this case, each directory or subdirectory corresponds to a previously stipulated group of task-specific, indication-specific or general applications. The relevant tools, or the file for said tools, are stored in the respective directory. This arrangement in directories provides a very simple way of making the respective tools available for querying or for referencing. If the medical data comprise image data, for example, then all tools which are stored in the image-data tools directory, for example, are referenced or provided for processing the medical data.

In this context, "provided" means that a link to the relevant position in the directory structure is created which is in turn linked to the activation element. The use of a file directory structure or a directory structure for the purpose cited above allows the division into groups to be implemented easily and inexpensively, since means for producing such a directory structure are available on almost every computer system available today.

In line with another embodiment of the invention, the determination of the required tools is implemented by a database query or a database. In this case, medical data, e.g. headwords or else meta data, that is to say details about file formats, for example, are put into database records and are associated with identifiers for the respective groups into which the tools have been classified.

By way of example, the database contains a data record in which one field contains the abbreviation ".jpg" and the other field in the same data record contains an identifier for a group of tools. If a directory structure has been chosen for implementing the groups, then a suitable identifier for the group is a path name or a path which indicates the precise position of the directory in the computer system's data memory. Such implementation of the tool grouping makes it a very simple matter for the groupings to be kept up to date. When the medical data have been captured, previously stipulated "strings" are extracted from the captured medical data, e.g. using a filter, and are sent to the database as a database query. The report from the database then delivers an identifier, that is to say a path, for a group, that is to say a directory, in which the respective tools can be found.

In line with another embodiment, the determination of the tools can also be implemented by a script. Suitable data structures in the script, e.g. hashes or arrays, model the association between medical data and the groups. The use of a script thus allows the use of a database to be rendered superfluous so as to be able to provide a very inexpensive and efficient alternative.

In another embodiment of the invention, the graphical design of the segments within the activation element areas can be set, that is to say the size composition and/or shape of the segments, for example. This allows the interface to be designed dynamically for the respective instance of application. Preferably, all steps in the method take place automatically.

In line with another embodiment of the invention, the size of the activation element area or the segments it contains is chosen in respect of the space requirement of the image data area. Thus, when viewing images or image material with a large space requirement it is possible to choose the activation element area or the segments to be so small that there is no overlap between the activation element area and the image data area, and in particular this makes it possible to ensure that the activation elements in the segments do not cover the image data area.

Another way of achieving the object is a UI controller. The UI controller is a device, e.g. a software module, which controls the presentation of the user interface, e.g. on a screen. In particular, the UI controller performs the function of presenting activation elements, which are linked to tools, in groups within an activation element area, the activation element area being one part of the user interface while what is known as the image data area is another. The UI controller comprises:

a determination module for determining which tools are required for processing captured medical data; preferably, the determination module interacts with a captured module, which is intended for capturing the medical data and which may be in the form of an external or internal module;

a presentation module, whose function is to present the activation elements in that segment within the activation element area which is associated with these activation elements, wherein the division of the activation elements is based on division of the tools associated with the respective activation elements, the division of the tools being in respect of medico-technical tasks or in respect of an indication and being implemented by a directory structure in which the tools are stored.

The determination module is a device which may be part of the UI controller, for example, but it may also be a separate device. Preferably, the determination module performs the task of analyzing the captured medical data according to previously stipulated data, e.g. filtering them according to headwords or filtering them according to appropriate meta data, e.g. abbreviations, which refer to the file format in which some of the medical data are present.

The presentation module can likewise be considered part of the determination module, but it may also be a separate device which is actuated directly by the UI controller. The presentation module calculates or determines the exact position of an activation element on the user interface. To be more precise, the presentation module receives information, e.g. from the UI controller, about the group with which the tool associated with the activation element is associated, so that the activation element can be shown or positioned in the relevant segment within the activation element.

In line with one embodiment of the invention, the tools, that is to say the processing of applications for processing medical data, for example, are combined into groups beforehand. This grouping reflects the context within which the respective tool is used. By way of example, grouping into task-specific, indication-specific and/or into general tasks is conceivable. Since each tool has at least one associated activation element, the grouping of the tools automatically also groups the respective activation elements.

The medical data include patient-related data, such as are provided by a conventional HIS system within a medical facility. In this case, the medical data are stored as data records in databases and are provided with information, such as a patient identification, text documents about medical history, image material and the like. Preferably, these medical data also contain meta data, as already mentioned above, which are provided in abbreviations, for example, and are able to give an indication of the respective file format in which the medical data are delivered. In line with one aspect of at least one embodiment of the invention, however, these meta data may also be embedded in the respective medical data or the data record as xml particles, for example. These xml data could contain information about the medical indication, for example.

Another embodiment of the invention provides a determination module which takes the captured medical data as a basis for determining which tools are required before processing these medical data. Preferably, these tools are determined by the determination module by analyzing the medical data. Preferably, the medical data are filtered according to previously stipulated headwords or other strings. When the determination module has found a data item which it knows within the medical data, one aspect of the invention involves this data item being used for a database query in a database. The database is provided with data records which associate the relevant medical data item with each group of tools (and hence also with the group of activation elements) or an identifier thereof. Preferably, the identifier for the group of tools (or activation elements) is a path under which the relevant tool can be found. The determination module uses the path found in this way to create a link or a reference file which the doctor or the user can use to activate the desired tool using the activation element. In this connection, the use of a database allows the associations between the medical data and the groups of tools to be kept up to date very easily. By way of example, newly added tools can easily be put in.

In line with another embodiment of the invention, the determination module can determine the association between the groups of tools and the medical data using a script too, as has already been described in connection with the method. In this case, the association between groups and medical data is implemented by suitable data structures, such as hashes or arrays. The use of a script allows the association to be implemented very inexpensively in this case, since an appropriate compiler is resident almost on every computer system available today.

In line with one embodiment of the invention, the grouping of the tools into indication-specific, task-specific and general tasks is implemented by a directory structure within the computer system. In this case, tools which are each used in the same context, that is to say when a particular indication is present, for example, are stored in the same directory. The associated activation elements are preferably also stored in the respective directories together with the tools. Almost every operating system on a computer system today provides options for creating and generating such a directory structure. The association between groups and medical data can therefore be obtained very inexpensively.

In line with another embodiment of the invention, the presentation module allows configuration of the geometrical form of the segments into which the activation element area is divided, of the activation element area itself and of the image data area. In this case, the doctor can select the image data area to be very large, e.g. for X-ray shots which show very many details. The activation element area is thereby presented in a correspondingly smaller form, so that the activation elements placed in the activation element area do not cover the image data area.

The inventive embodiments of the method which are described above may also be in the form of a computer program product, with the computer being prompted to carry out the inventive method described above and the program code thereof being executed by a processor.

An alternative way of achieving the object provides a storage medium which is intended for storing the computer-implemented method described above and can be read by a computer.

BRIEF DESCRIPTION OF THE DRAWINGS

The detailed description of the figures which follows discusses example embodiments, which are to be understood as nonrestrictive, with their features and other advantages with reference to the drawings, in which:

FIG. 1 shows a synoptic illustration of the flow of data and of modules based on an example embodiment of the invention.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an embodiment, based on the invention, of a computer-based medico-technical appliance 100 for processing medical data 130. The user interface 110 is in a form such as may appear on a monitor or a screen (not shown) based on one embodiment of the invention. In this case, the image data area 120 is intended for presenting medical data, e.g. X-ray images or other image material. The activation element area 150 is divided into segments 140a to 140c, which segments contain activation elements 180a, representing a reference to the relevant tool 180, on the basis of context. By way of example, the segment 140a contains task-specific activation elements, the segment 140b contains indication-specific activation elements, while the segment 140c contains activation elements which refer to tools for performing general tasks.

The geometrical positioning of the activation elements 180*a* within the correct or associatable segment is achieved by the determination module 115*a*. In this case, the presentation module 115*b* is shown as part of the UI controller but may also be an autonomous device. The UI controller holds information ready regarding the size and position at which the segments and/or the activation element area and/or the image data area need to be presented.

The determination module 115*a* provides the UI controller and, ultimately, naturally also the presentation module 115*b* with information about the group association of the activation element 180*a*. This information is then converted in the UI controller into the actual geometrical position of the activation element in the relevant segment.

The medical data 130 are used as a patient-related data record in preferably electronic form, e.g. by an HIS system, e.g. in a hospital. The medical data include a patient ID, information about the medical history, such as is usually stored with the ending ".doc" in text documents, or in appropriate electronic forms. The data records will generally naturally also contain image material, such as X-ray images, in an appropriate graphical format, such as DICOM data records. The details about the data format are referred to as meta data 130*a* in this connection. However, the meta data may also contain xml markers, for example, this allowing additional information, e.g. about the indication to be embedded in the medical data. The total data record or portions thereof is/are captured by the data capture device 190 and stored in a buffer store, for example.

In line with one embodiment of the invention, the data capture device can also parse the medical data and thus put it into a form which allows further processing by the determination module 115*a*. The determination module 115*a* analyses the medical data, e.g. by filtering the data according to known headwords or other strings, and starts a database query in a database 195 when a string which is known to the determination module 115*a* is present. Within a data record 160, the string found in this way is associated with a group of tools or with an identifier for a group of tools.

In line with one embodiment of the invention, this identifier includes a path which points to the tool which may be or is required for processing a medical data item characterized by this string. In this case, the path found in this way refers to a directory within a directory structure 160. The directory 160 models the group in a manner of speaking and contains the tools 180 required for processing the medical data of the type denoted by the string found and preferably also the activation element 180*a* which is associated with this tool 180. The determination module 115*a* captures this path and uses it to construct a link or a reference file which is linked to the activation element 180*a*. To be able to prompt graphical representation of the reference file, the determination module 115*a* sends the UI controller 115 a reference for the relevant activation element, this reference preferably matching the path under which the tool can be found.

In conclusion, it should be pointed out that the description of the invention and the example embodiments are in principle intended to be understood to be nonrestrictive in respect of a particular physical implementation of the invention. In particular, it is obvious to a person skilled in the relevant art that the invention can be implemented partly or completely in software and/or hardware and/or in a manner distributed over a plurality of physical products—in this case particularly also computer program products.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDS; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for dynamically generating a user interface in a computer-based, medico-technical system including at least one image data area for displaying medical data and at least one activation element area, divided into segments, for displaying a multiplicity of activation elements divided into groups, wherein a respective segment of the activation element area is associated with a respective group of activation elements on the basis of a configurable association mechanism, an activation element being intended for activating at least one tool associated with it, the method comprising:
capturing medical data relating to a patient;
determining which different tools are required for processing the captured medical data; and
dynamically generating the user interface by presenting selected activation elements associated with control of the different required tools in the segment of the activation element area of the user interface associated with the selected activation elements, the division of the activation elements being based on division of the tools associated with the respective selected activation elements, the tools being divided in respect of at least one of medico-technical tasks and an indication, wherein the determination of the required tools is implemented by a database query in a database, wherein, in the database, a respective group of at least one of activation elements and tools has at least one associated data item from the medical data via an identifier.

2. The method as claimed in claim 1, wherein the medical data also include meta data and wherein the required tools are determined using at least some of the meta data.

3. The method as claimed in claim 1, wherein the determination of the required tools is implemented by a script.

4. The method as claimed in claim 1, wherein the multiplicity of the groups of tools is implemented by a hierarchic directory structure.

5. The method as claimed in claim 1, wherein further comprising setting at least one of a size, a shape and a position of at least one of the segments, the activation element areas and the image data area.

6. The method as claimed in claim 1, wherein at least one of the segments and the activation element area are positioned such that the image data area is not covered by activation elements.

7. The method as claimed in claim 1, wherein the tools include computer-based medico-technical applications for the processing of medical data.

8. The method as claimed in claim 1, wherein the medical data include medical image material.

9. A computer program product which can be loaded directly into a memory in a computer, comprising program code segments in order to carry out all the steps of a method as claimed in claim 1 when the program is executed in the computer.

10. A computer readable medium including program segments for, when executed on a computer device, causing the computer device to implement the method of claim 1.

11. The method as claimed in claim 1, wherein dynamically generating the user interface includes generating a context-dependent graphical user interface for controlling a medico-technical apparatus, the context being derived from the medical data relating to a patient.

12. The method as claimed in claim 1, wherein dynamically generating the user interface includes generating the user interface based on the captured medical data.

13. The method as claimed in claim 2, wherein the determination of the required tools is implemented by a script.

14. The method as claimed in claim 2, wherein the multiplicity of the groups of tools is implemented by a hierarchic directory structure.

15. A user interface (UI) controller for controlling a user interface in a computer-based, medico-technical system, the user interface including at least one image data area for displaying medical data and at least one activation element area, divided into segments, for displaying a multiplicity of activation elements divided into groups, wherein a respective segment of the activation element area is associated with a respective group of activation elements on the basis of a configurable association mechanism, with an activation element being intended for activating at least one tool associated with it, the UI controller comprising:

a processor coupled to a memory;
a determination module that determines which different tools are required for processing the captured data; and
a presentation module that, in response to the determined tools required for processing the captured data, presents the activation elements associated with the different required tools in that segment of the activation element area in the user interface associated with these activation elements, wherein
the division of the activation elements is based on division of the tools associated with the respective activation elements, the division of the tools being in respect of at least one of medico-technical tasks and an indication and being implemented by a directory structure in which the tools are stored, and
the determination of the required tools is implemented by a database query in a database, wherein, in the database, a respective group of at least one of activation elements and tools has at least one associated data item from the medical data via an identifier.

16. A computer-based medico-technical system, comprising a screen on which at least one activation element for at least one tool is presented and which is controlled by way of a UI controller as claimed in claim 15.

* * * * *